US011270520B2

(12) United States Patent
Hawkins et al.

(10) Patent No.: US 11,270,520 B2
(45) Date of Patent: Mar. 8, 2022

(54) INTRA-ORAL SCANNING DEVICE WITH ACTIVE DELETE OF UNWANTED SCANNED ITEMS

(71) Applicant: D4D Technologies, LLC, Richardson, TX (US)

(72) Inventors: Jessica Hawkins, Richardson, TX (US); Justin G. Graham, Wylie, TX (US)

(73) Assignee: D4D Technologies, LLC, Richardson, TX (US)

(*) Notice: Subject to any disclaimer, the term of this patent is extended or adjusted under 35 U.S.C. 154(b) by 21 days.

(21) Appl. No.: 16/791,387

(22) Filed: Feb. 14, 2020

(65) Prior Publication Data

US 2020/0265653 A1 Aug. 20, 2020

Related U.S. Application Data

(60) Provisional application No. 62/805,982, filed on Feb. 15, 2019.

(51) Int. Cl.
*G06T 19/20* (2011.01)
*G06T 17/10* (2006.01)

(52) U.S. Cl.
CPC ........... *G06T 19/20* (2013.01); *G06T 17/10* (2013.01); *G06T 2207/10028* (2013.01)

(58) Field of Classification Search
None
See application file for complete search history.

(56) References Cited

U.S. PATENT DOCUMENTS

| 10,064,553 | B2 | 9/2018 | Fisker et al. |
| 2014/0212832 | A1* | 7/2014 | Fisker ................. G06T 7/55 433/29 |
| 2015/0297324 | A1 | 10/2015 | Tchouprakov et al. |
| 2015/0374460 | A1 | 12/2015 | Sachdeva et al. |
| 2018/0137608 | A1* | 5/2018 | Carlson ................. G06T 11/008 |
| 2018/0221110 | A1 | 8/2018 | Boltunov et al. |
| 2018/0308286 | A1 | 10/2018 | Graham et al. |
| 2019/0046302 | A1 | 2/2019 | Li et al. |

FOREIGN PATENT DOCUMENTS

WO 2018170030 A1 9/2018

OTHER PUBLICATIONS

International Search Report and Written Opinion, PCT/US2020/018458, dated Jun. 12, 2020.

* cited by examiner

*Primary Examiner* — Yanna Wu
(74) *Attorney, Agent, or Firm* — Scheef & Stone, LLP; Robin L. Barnes; John G. Fischer (57) ABSTRACT

An intra-oral scanning device and system are augmented to provide an active delete (or filter) tool. The tool automatically detects and deletes unwanted items and artifacts capturing as the scan is being done. The technique provides a better user experience by automatically removing items the deletion of which that may otherwise be time-consuming, frustrating, or impossible for the user to delete any other way.

14 Claims, 10 Drawing Sheets

INTRA-ORAL SCANNING DEVICE WITH ACTIVE DELETE OF UNWANTED SCANNED ITEMS

BACKGROUND OF THE INVENTION

Technical Field

This disclosure relates generally to scanning devices and methods and, in particular, to enhanced data capture and display of data captured by an intra-oral scanner.

Brief Description of the Related Art

Previously-described dental imaging systems enable a user to scan patients intra-orally and produce a three-dimensional (3D) digital model of the dental anatomy. Such devices are used in a standalone manner or as part of a computer-aided design and manufacture (CAD/CAM) system. A CAD/CAM system typically uses dental CAD software executing on a laptop or desktop machine, optionally together with specialized milling machine hardware driven by machine control CAM software. The dentist first prepares a patient's damaged tooth anatomy (using standardized dental practices) to receive a dental restoration including, but not limited to, an inlay, an onlay, a veneer, a crown or a bridge. Once the preparation has been made, the dentist uses the scanner described and illustrated herein to capture a digital impression of a patient's dental anatomy. Once the digital impression has been captured the dentist is presented with an "initial proposal" restoration by the automated CAD software. This initial proposal preferably automatically selects an appropriate tooth anatomy, and it sizes it to fit onto the preparation and within the patient's existing "good" anatomy. This initial proposal is then customized by the dental professional, typically using specialized software tools to adjust and modify the design, with the goal of ultimately achieving an optimized design that fits into the patient's anatomy. Once the final 3D model of the tooth has been achieved, it is sent electronically to a milling machine (or third party), which then generates the actual restoration from the design.

In operation, scanning software resident on an associated computer (e.g., desktop, laptop, or the like) extracts a 3D point cloud from the captured data, aligns the 3D point cloud to previously captured data, and renders to a display screen (or other output). This process is repeated as the user continues to scan. The system then allows the user to bring the restored anatomical data into a design tool. Through the use of the software, the user then designs a restoration (e.g., a crown) to fit the anatomical features.

In the above-described approach, the scanned object typically is represented in software as a collection of discrete, 3D samples that approximate the real, continuous surface (such as the surface of a tooth.) These 3D samples may be organized into a voxel grid, or they may be simply a list of 3D points. Each point may carry with it a "weight" representing the data density at that location. As the user spends time scanning, more data is collected, and the weight generally increases as data density increases. The weight may also be understood as the scanning algorithm's certainty that the 3D samples are a good representation of the true surface; as the user spends time collecting data, this certainty tends to increase.

While existing scanner devices provide satisfactory results, during the scanning process the user may accidentally scan items they wish to be deleted. For the dental user, these items include, for example, fingers, lips, cheek, dental instruments, and tongue. After the scan is complete, the user may go back and manually erase these items and other scanning artifacts that do not represent the desired anatomy or object. This known deletion process, however, is time-consuming and often frustrating for the user, and, depending on the nature of the artifact or its location in the scan, sometimes it is not possible for the user to delete it without adversely impacting the integrity of the portions of the scan that represent the true object of interest.

BRIEF SUMMARY

An intra-oral scanning device and system are augmented to provide an active delete (or filter) tool. The tool automatically detects and deletes unwanted items and artifacts capturing as the scan is being done. The technique provides a better user experience by automatically removing items the deletion of which that may otherwise be time-consuming, frustrating, or impossible for the user to delete any other way.

The foregoing has outlined some of the more pertinent features of the subject matter. These features should be construed to be merely illustrative.

BRIEF DESCRIPTION OF THE DRAWINGS

For a more complete understanding of the disclosed subject matter and the advantages thereof, reference is now made to the following descriptions taken in conjunction with the accompanying drawings, in which.

DETAILED DESCRIPTION

The following provides background concerning intra-oral scanning techniques, devices and systems in which the techniques of this disclosure may be implemented.

Figure 1:
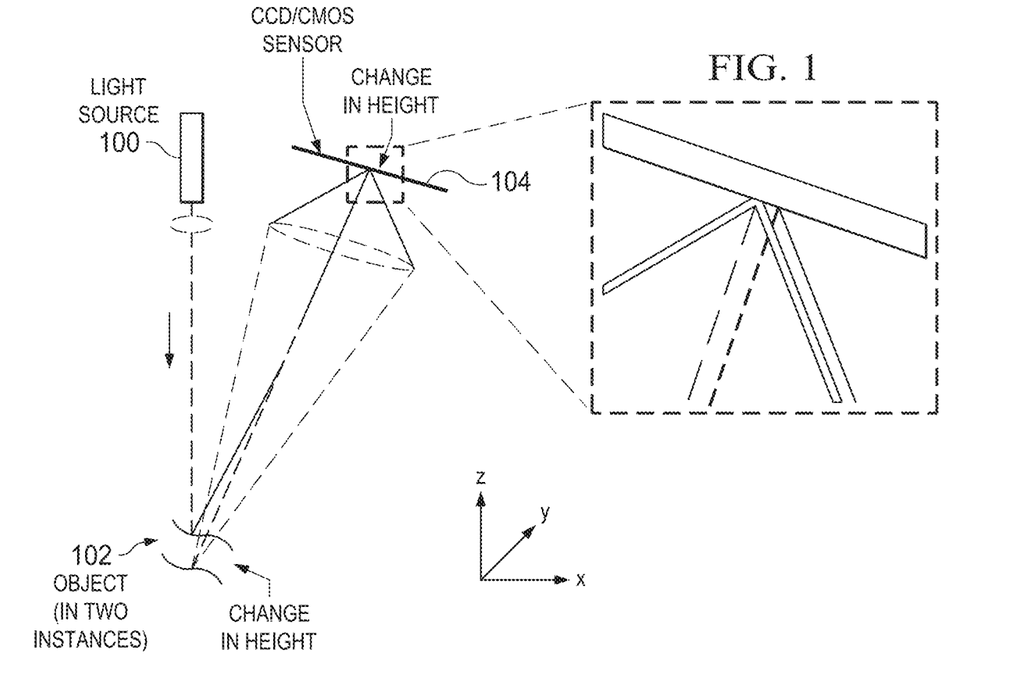
FIG. 1 illustrates basic components and geometry underlying 3D triangulation.

The principles behind structured light based 3D triangulation are explained in various works. The underlying principles are described with respect to FIG. 1, which illustrates a light source 100 directed to an object 102, with the reflection being captured a charge coupled device (CCD) imaging surface 104. This illustrates the basic components and principles behind 3D triangulation in an intuitive manner. In this approach, a change in height due to object topography is registered as a deviation of a projected point onto a charge coupled device (CCD) imaging surface. In operation, a laser pattern is projected with the help of an LCOS (i.e. liquid crystal on silicon) device. In particular, a sequence of a set of lines is generated by the lines reflected from LCOS to form a set of planes, or, if distortion is involved (as typically is the case when implemented), a set of conical or ruled surfaces.

Figure 2:
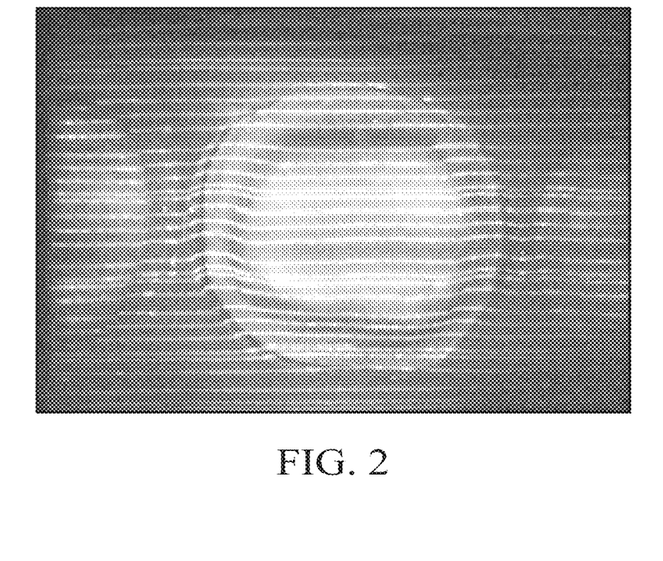
FIG. 2 is a known technique to project laser pattern lines onto a preparation area using an intra-oral hand-held wand device.
Figure 3:
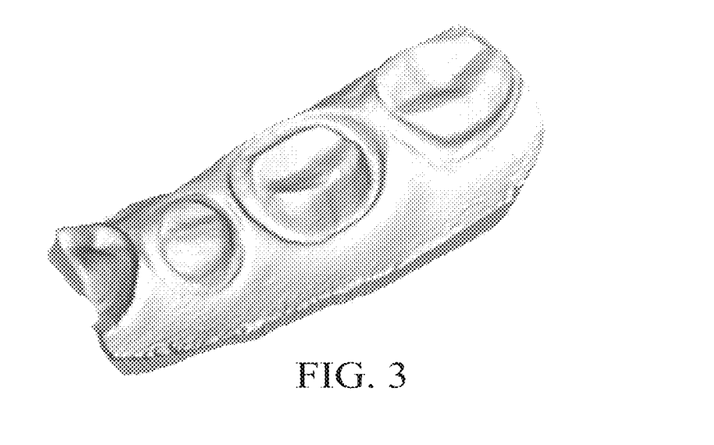
FIG. 3 illustrates a 3D generated model created by processing the partially-illuminated pattern lines.

FIG. 2 illustrates a pattern projected onto a preparation area. In an analogous manner, each point in the camera CCD frame corresponds to a line in space that passes through the imaging center or focal point. Because preferably the LCOS and the camera are laterally separated, the point of intersection between each laser surface generated by a single LCOS pixel and each line of sight is well-defined. Thus, by knowing the pixel coordinates on the camera matrix and the shape of the laser surface, it is possible to obtain coordinates of a 3D point corresponding to that pixel. When laser lines are projected onto the surface of the scanned object, the image of those lines in the camera plane defines a set of 3D points corresponding to the object surface. To obtain the shape of the surfaces formed to each laser line, a calibration procedure is performed. A camera lens calibration is performed by taking an image of a checkerboard pattern, with a set of intrinsic camera parameters (such as focal length and lens distortion) estimated as a result. From this, an exact direction of a ray corresponding to each camera pixel is established. To determine the shape of the laser surfaces, a set of planes located at the known distances with known orientation are scanned. Each line projected onto each successive plane forms an image on the CCD matrix, represented as a set of pixels and, because for each pixel the corresponding direction and the actual distance to the calibration plane are known, the set of 3D coordinates forming a line of intersection between a laser surface and calibration plane are known as well. Interpolation between successive lines produces the shape of the laser surface, represented by the final generated 3D model shown in FIG. 3.

The frames used to capture the data for the 3D model are partially-illuminated frames (such as shown in FIG. 2, wherein the LCOS paints a series of lines in a pattern). To facilitate the operation of the device and provide live video as feedback to the operator (as well as the 3D-computed data), a sequence of patterns throughout which full illumination frames are selectively interspersed. A full illumination frame involves all or substantially all lines being turned on, as compared to the partially-illuminated approach shown in FIG. 2, wherein only some lines are projected. In a full illumination frame, in effect there is no pattern. The partially-illustrated frames provide the data from which the 3D coordinates of the surface are determined. A technique for rendering frames in this manner is described in U.S. Pat. No. 7,184,150, the disclosure of which is incorporated herein by reference. In contrast, the full illumination frames are used for texturing the 3D model generated by the partially-illuminated frame data. In one sequence, a first set (e.g., six) pattern frames are used, interspersed with a second set (e.g., three) illumination frames, for a sequence total of nine total CCD frames. A software traffic shaper is then used to separate captured frames in two streams, namely, a live preview stream, and a data processing stream from which the 3D model is generated. If necessary, e.g., for computational or storage efficiencies, the live preview stream can give up priority and drop some frames when the CPU work load exceeds a certain limit.

In one embodiment, the same light source (e.g., a blue laser) is used to generate both the first series of frames and the second series of (interleaved) frames, and a monochrome sensor is used. If it is desired to output a color video preview, one or more other light sources (e.g., a red laser, a green laser, or some combination) are used to vary the color of the full illumination frames. Thus, in one alternative embodiment, there are three different light sources (blue, red and green), with the resulting data returned from these full illumination frames then being used to provide a color video preview. As yet another alternative, full illumination frames are generated using a source of monochrome light, and a color sensor is used to receive the reflected data (to generate the color video preview). Still another alternative to generate a color video image is to use full illumination red and green frames with a partial illumination blue frame. Other light sources (e.g., a red/green laser or even an LED) may obviate the full illumination blue frame. Another possibility is to use red as the additional color (leaving out the green, or vice versa), and then processing the resulting data to generate a pseudo-color video stream. When the approach uses the red, green and blue laser, the scanner may be used to generate a simplified optical coherence tomography (OCT) scan using discrete lasers instead of a single broadband source, or a swept source.

Figure 4:
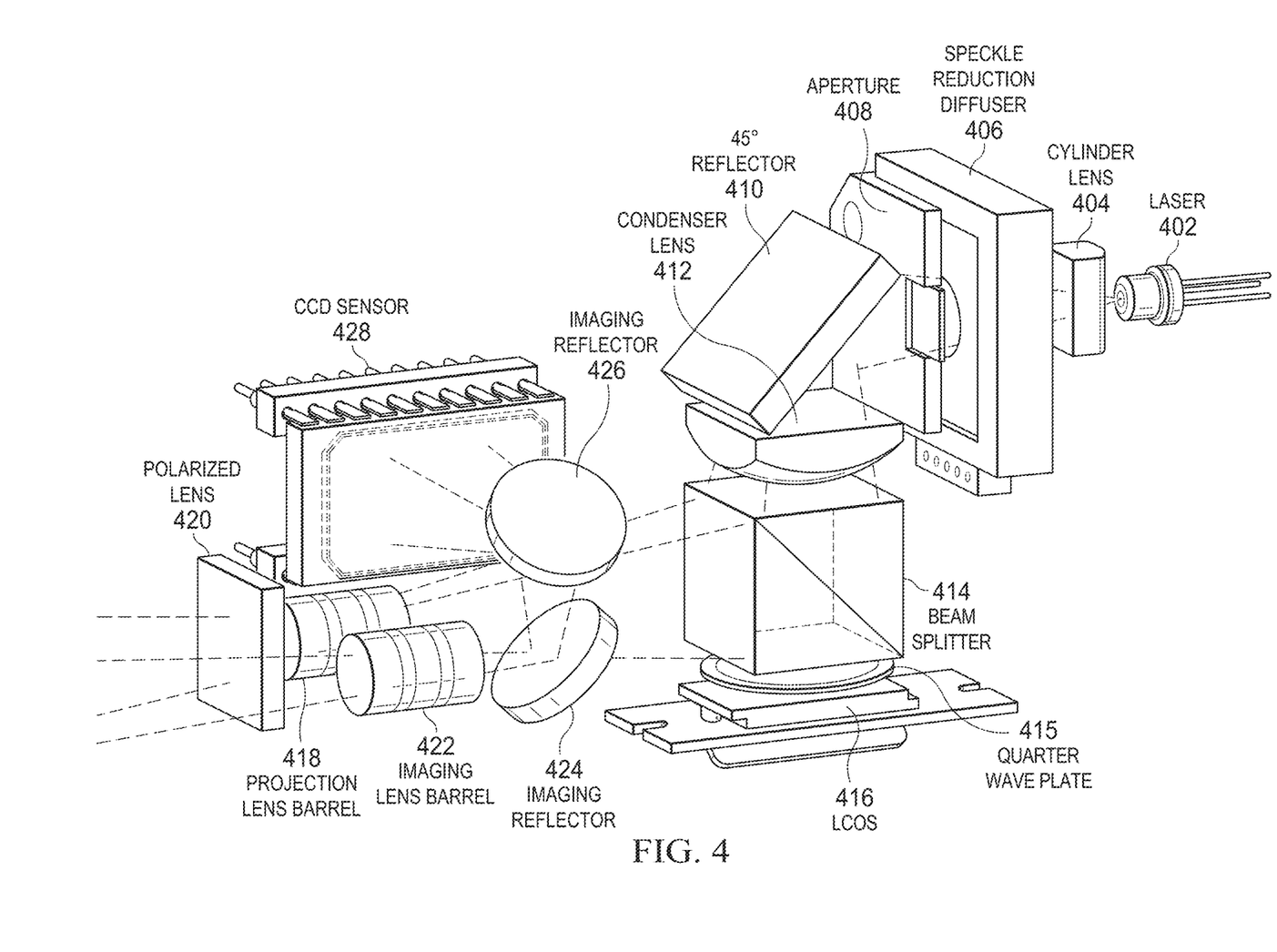
FIG. 4 illustrates an optical sub-system of an intra-oral scanning device with its outer housing removed.

FIG. 4 illustrates an embodiment of an optical sub-system of an intra-oral device with its outer housing removed. The primary imaging components of the optical sub-system 400 include a laser 402, a cylinder lens 404, a speckle reduction diffuser 406, an aperture 408, a reflector 410, a condenser lens 412, a beam splitter 414, a quarter wave plate 415, the LCOS device assembly 416, a projection lens barrel assembly 418, and a polarized lens 420. A return (imaging) path comprises imaging lens barrel assembly 422, first and second imaging reflectors 424 and 426, and the CCD sensor 428.

Without meant to be limiting, the laser is a blue laser device with a wavelength of 450 nm, and thus the optical path for the projection side is polarization-based. In this embodiment, projection is achieved with the LCOS device 416 having a resolution of 800 by 600 pixels and a pixel size of 8.0 um. The speckle reduction diffuser (a de-speckle component) is used to eliminate the speckle issues otherwise caused by using a laser as the light source. Using a laser (instead of, for example, an LED light source) produces a much brighter projected pattern which, in turn, allows the scanner to image intra-orally without powder.

Figure 5:
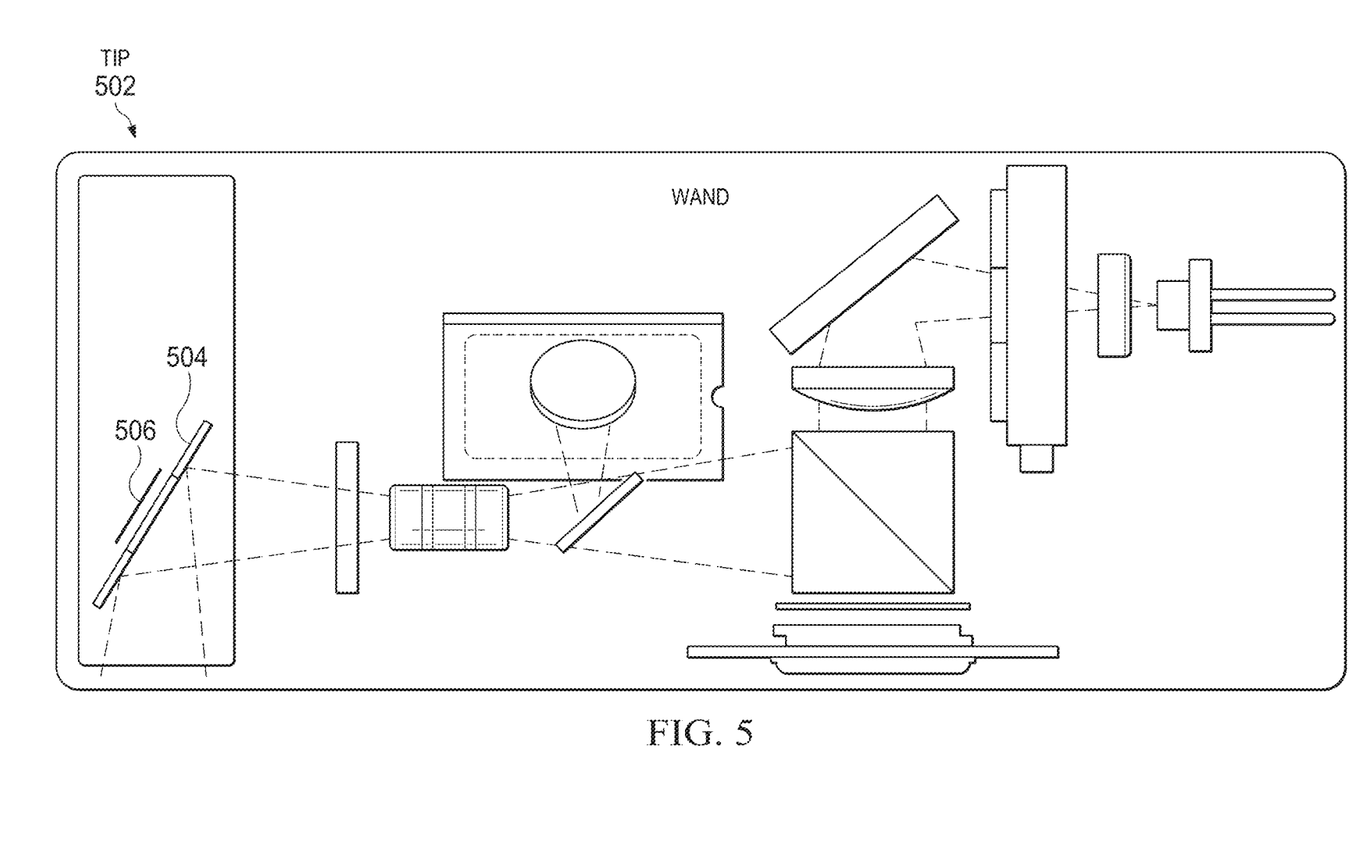
FIG. 5 is an elevation view of the intra-oral scanning device.

As seen in FIG. 5, the intra-oral device 500 is configured as a hand-held wand that includes a tip portion or "tip" 502. The tip 502 includes a mirror 504 and preferably no additional glass windows; the mirror 504 reflects the projection path from a long axis of the device (the optical sub-system shown in FIG. 4) towards the target area being scanned, and that receives the imaging path data returned from the target area. The returned data is forwarded down the long axis of the device, where it is imaged by the CCD sensor device. By using a mirror 504 in the tip 502, the possibility of a surface near the target area being contaminated with dirt or fluid is reduced. This is desirable, as any contamination on a glass window or prism surface may be close to (or within) a focused region of the optical path, and therefore may result in erroneous measurements. The reflecting mirror 504 is outside the focus region, and thus any slight imperfections or debris on its surface will not result in erroneous data measurements. Preferably, the tip 502 is removable from the rest of the wand housing, and the mirror is heated (with an active heating element 506) to prevent fogging of the optical surfaces while the device is being deployed intra-orally. The heating element may be a metal conductive element that is supported in a molded plastic housing and that receives current from other wand electronics. Any other type of heating element may be used. In this manner, multiple tips (the others now shown), each with varying mirror angles and sizes, may be implemented with a single wand body that includes the optical sub-system shown in FIG. 4. In this manner, different tips may be used for different scanning scenarios, such as scanning posterior preparations in small patients, or more challenging situations where a steeper viewing angle is required.

Figure 6:
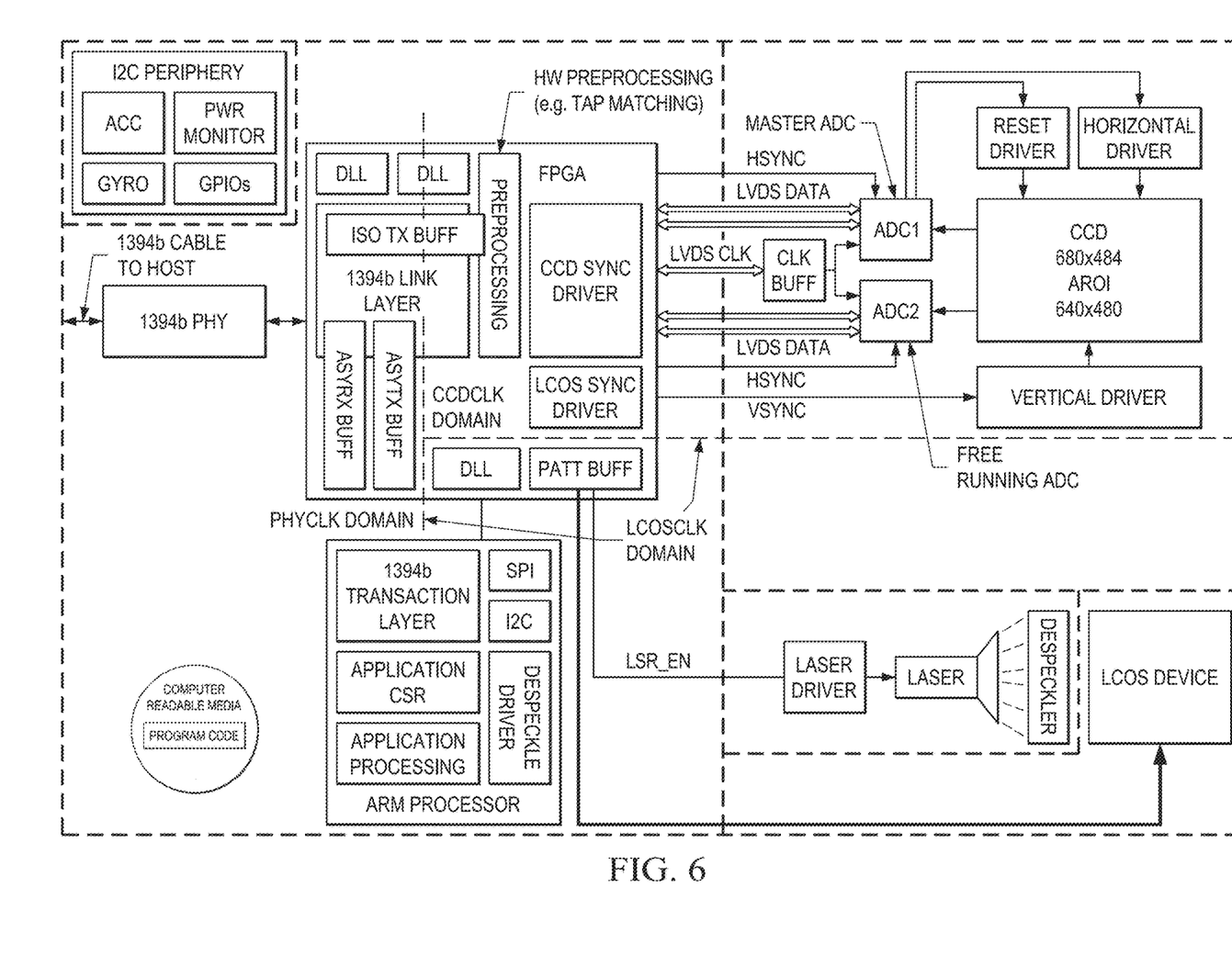
FIG. 6 is an embodiment of system architecture to control the hand-held intra-oral device.

FIG. 6 illustrates system architecture for the wand. In this implementation there are three (3) subsystems, namely, an imaging sub-system, a projection/illumination sub-system, and a periphery sub-system. Preferably, imaging is achieved by an over-clocked dual-tap CCD with an active resolution of 648 by 484 pixels, and a pixel size of 9 um.

In this embodiment, which is not intended to be limiting, the system architecture comprises a tightly-integrated IP FPGA core containing an IEEE 1394b 5800 link layer, CCD/ADC synchronizers, the LOCS and illumination synchronizer. Cross-clock domain FIFOs are implemented to synchronize the CCD exposure/LCOS projection/CCD readout sequence to the IEEE1394 bus clock, which is 125 us or 8000 Hz. The FPGA is assisted by an ARM processor, implementing the IEEE1394b transaction layer and various housekeeping system tasks, such as running an I2C periphery priority task scheduler. The FPGA implements deep FIFOs for asynchronous packet reception and transmission and likewise for the CCD video data, which is sent as isochronous packets. It also implements a prioritized interrupt mechanism that enables the ARM processor to de-queue and en-queue IEEE1394 asynchronous packets and to complete them according to the bus transaction layer specification and various application requirements. The bulk of the housekeeping work in the system originates in user space software, ends up as an asynchronous packet in the ARM processor and is dispatched from there through either I2C or SPI to the appropriate peripheral component. The software is designed to maintain the hardware pipelining while running within a non-real time operating system (OS), such as Microsoft® Windows and Apple® OS/X. Other operating systems such as Android or iOS® may be used.

Figure 7:
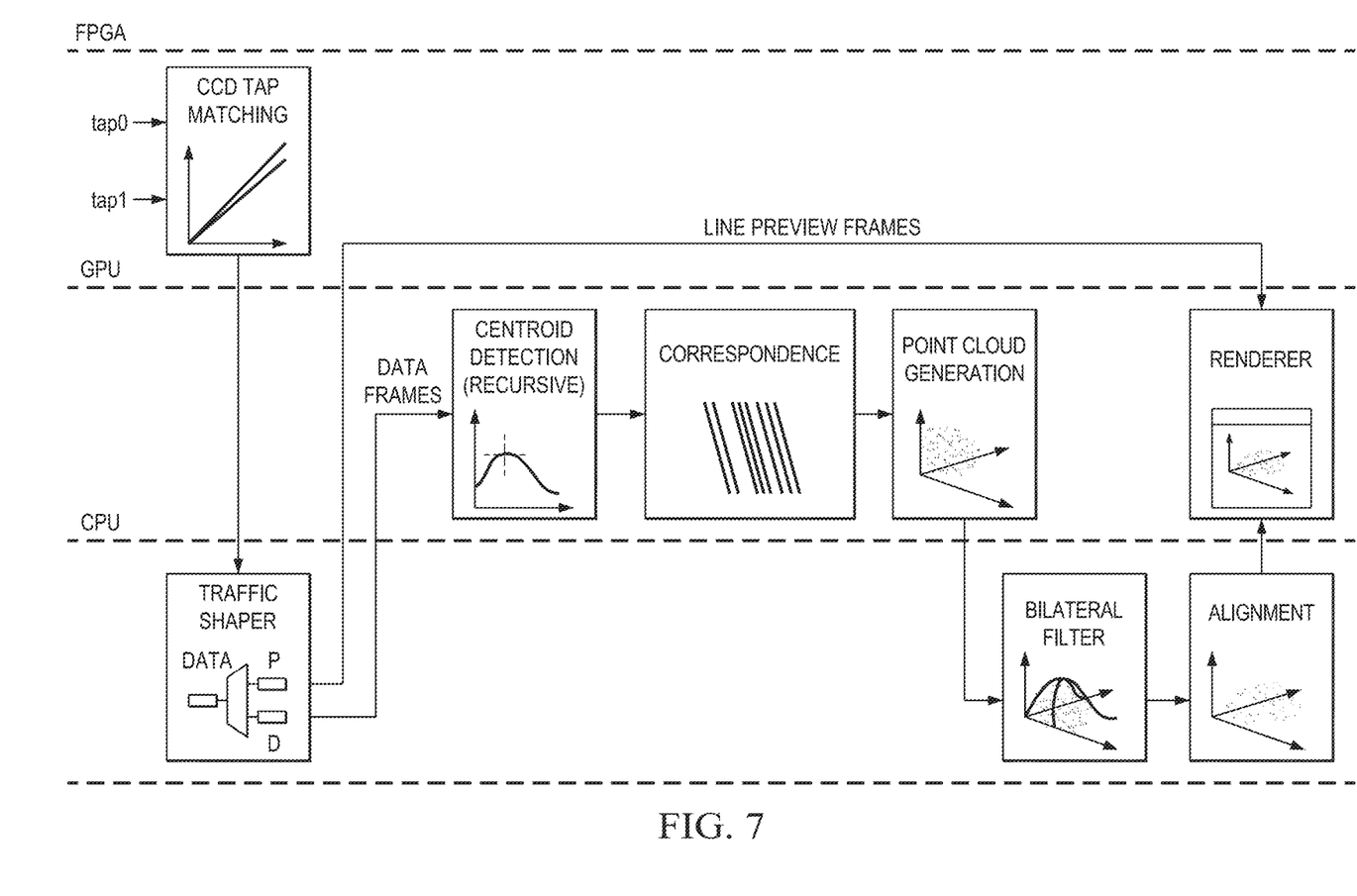
FIG. 7 illustrates a 3D pipeline processing approach implemented in the device.

In this embodiment, and to provide the required data quality at a desired rate, the imaging system preferably is comprised of a slightly over-clocked dual tapped CCD. The CCD is 680 by 484 pixels containing some dark columns and rows for black offset correction and is specified to have 57 dB of dynamic range at a pixel clock of 20 MHz with a maximum pixel clock of 30 MHz. The projection and illumination subsystem comprises LCOS device, a laser diode driver, a 450 nm blue laser diode and an optical de-speckling device. As illustrated in FIG. 7, preferably data is processed in a pipeline distributed across several computing resources. In this approach, data from the CCD ADCs, 8 bit per pixel, is first run through a tap matching block where both taps are linearized and matched according to a look up table. This implies a previous calibration step. The traffic shaper separates the data into live preview and 3D processing input frames. The 3D processing input frames contain projected patterns. On the GPU these frames are first run through a centroid detector implemented as a recursive sub-pixel edge detector, a correspondence block, and finally a point cloud generation block. This output is then run on the CPU side through a bilateral filter for data smoothing, and through an alignment block to stitch scans together. This processing distribution allows for running alignment in a pipelined fashion with 3D point cloud generation happening in parallel.

Preferably, fast imaging is used to allow minimization of errors (e.g., due to operator hand jitter). In one embodiment, good results were obtained with a live preview window of approximately 20 frames per second, coupled with approximately 15 frames per second for the 3D data.

Figure 8:
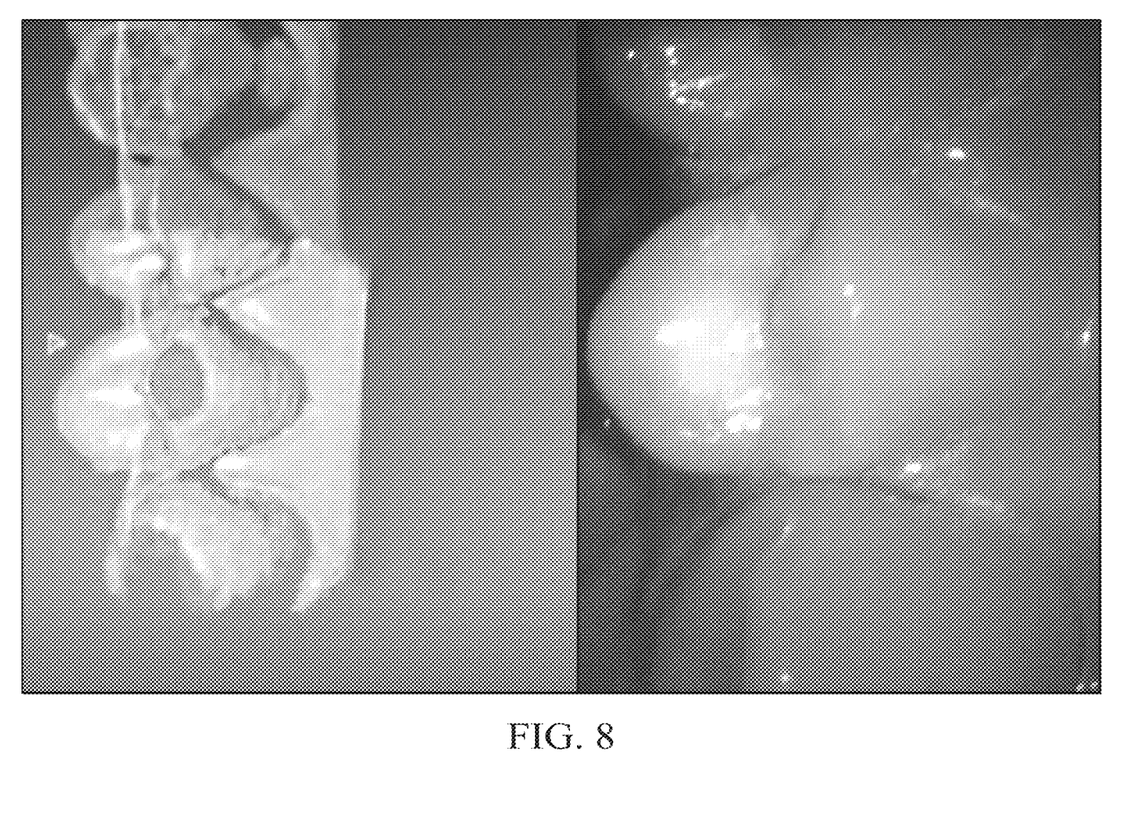
FIG. 8 illustrates the rendering of a textured 3D model juxtaposed against a live video feed provided by implementing a scan using the intra-oral scanning device.

A representative display interface is used to display the 3D model, on the one hand, and the live video preview window, on the other. FIG. 8 illustrates a representative screen grab from a juxtaposition of these views. These views may be juxtaposed in any convenient display format (e.g., side-by-side, above-below, as an overlay (or "3D texture" view), or the like).

The above-depicted optical system for the scanner is not intended to be limiting. An alternative configuration is described, for example, in U.S. Publication No. 2019/0046302, titled "Intra-oral scanning device," which application is commonly-owned, and the disclosure of which is hereby incorporated by reference.

Active Delete/Filtering Unwanted Items

In dental CAD/CAM applications as described above, a 3D model may be provided representing the upper or lower arches. FIG. 8 depicts a representative example. This model may be a 3D surface, for example, a surface composed on connected triangles where each triangle is made up of three 3D points along with a normal. The surface may also be textured with either a monochrome or color image superimposed on that surface. A technician may use this model to design a restoration that may be subsequently manufactured. These types of 3D models are most easily obtained through the use of an intra-oral scanner described and depicted above. A 3D intra-oral scanner is able to obtain 3D surface information as well as capture monochrome or color images that can then be superimposed on the 3D model.

As noted above, however, during the scanning process the user (e.g., a dentist, a technician, etc.) may accidentally scan items they wish to be deleted. For the dental user, these items include, for example, fingers, lips, cheek, dental instruments, and tongue.

According to this disclosure, the software routines (including those that are used to display the 3D model) are enhanced to provide an automated "active" delete function/feature. This feature may be activated by a default configuration setting, or it may be selected by the user (e.g., the technician performing the scan). When this feature is activated and used (e.g., with the 3D model displayed on the screen), unwanted/undesirable items, objects and other artifacts are automatically "deleted" (filtered) from the model that is being rendered on the display screen.

The active delete function typically occurs within the software executing on a computing device, and these operations (as defined further below) typically result in updating the version of the 3D model being rendered on the display.

As noted above, during scanning software resident on an associated computer (e.g., desktop, laptop, or the like) extracts a 3D point cloud from the captured data, aligns the 3D point cloud to previously captured data, and renders to a display screen (or other output). This process is repeated as the user continues to scan. The scanned object is represented in software as a collection of discrete, 3D samples that approximate the real, continuous surface (such as the surface of a tooth.) These 3D samples may be organized into a voxel grid, or may be simply a list of 3D points. Each point may carry with it a "weight" representing the data density at that location. As the user spends time scanning, more data is collected, and the weight is generally increased as data density increases. The weight also may be understood as the algorithm's certainty that the 3D samples are a good representation of the true surface; as the user spends time collecting data, this certainty tends to increase.

Preferably, the active delete approach herein leverages two (2) separate mechanisms to delete unwanted items. The first approach uses "line of sight" deletion, whereby the algorithm iteratively decreases the weight of 3D samples that it (the algorithm) determines are likely to be erroneous. Once the weight is below a threshold, the weight is set equal to zero, thereby causing the corresponding sample to be deleted. The second approach—referred to as "immediate deletion"—immediately deletes 3D samples that the algorithm is confident are erroneous. Immediate deletion is equivalent to setting the weight of these 3D samples to zero. This latter mechanism preferably is used for 3D samples that intersect the body of the scanner and for disconnected components (described in more detail below). Using both mechanisms together provides significant benefits. The first mechanism is useful when it is more advantageous to delete erroneous data slowly, such as when the erroneous data is resting directly against the desired surface. In this case, the algorithm must proceed carefully because the true surface is not yet known. The second mechanism, as its name implies, provides more immediate deletions, as the need for further data collection (to make the deletion determination) is not necessary. As noted, this would be the case for artifacts or other items that are clearly not part of the scan.

Each of these mechanisms is now described in further detail.

Line-of-Sight Deletion

In practice, the user will move the camera freely to collect data from different angles and positions. Therefore, a usual part of 3D scanning is that new 3D samples must be aligned to the existing 3D samples. Alignment is the process of finding a transformation (rotation and translation) from the world coordinates, in which all the existing 3D samples exist, to the camera coordinates, in which the new 3D samples exist. Additionally, the camera itself may contain distortions, which are typically measured at the time of calibration. The existing 3D samples are referred to as the "point cloud," and the new 3D samples are referred to as "scan points."

The following is one preferred algorithm for implementing the line-of-sight delete functionality. A basic goal of line-of-sight deletion is to find any points in the point cloud that are along a line-of-sight from the camera to any scan point. If any such points are found, the weights of these point cloud points are decreased until deletion. To make the line-of-sight comparison, the algorithm preferably operates as follows. The algorithm begins by finding all points in the point cloud within a volume that approximates the viewing frustrum. In 3D computer graphics, the view frustum (also called viewing frustum) is the region of space in the modeled world that may appear on the screen; it is the field of view of a perspective virtual camera system. These points can be found by an exhaustive search or through knowledge of the underlying point cloud data structure, such as a voxel grid. Then, and for each of these points, the algorithm transforms its position from world coordinates to camera coordinates, and applies any known camera distortions, thereby finding a pixel position where the point would have been seen by the camera. Thereafter, the algorithm compares each of these points to the scan point that was seen at that pixel, if any. For any of these points that are closer to the camera than the scan point at the corresponding pixel, its weight is decreased, say by a factor S. Then, if the weight of any point in the point cloud falls below a threshold, that weight is set equal to zero. This is equivalent to deleting the point. The weighting factor S may vary depending on the geometry. For example, if the point cloud point is very close to the corresponding scan point, a lower value of S may be used, in effect deleting the point cloud point more slowly. As another example, if the normal vector of the point cloud point is close to being perpendicular to the camera viewing direction, a lower value of S may be used, because this geometry is especially sensitive to camera calibration or motion errors. In addition, the threshold itself may be configurable.

Figure 9:
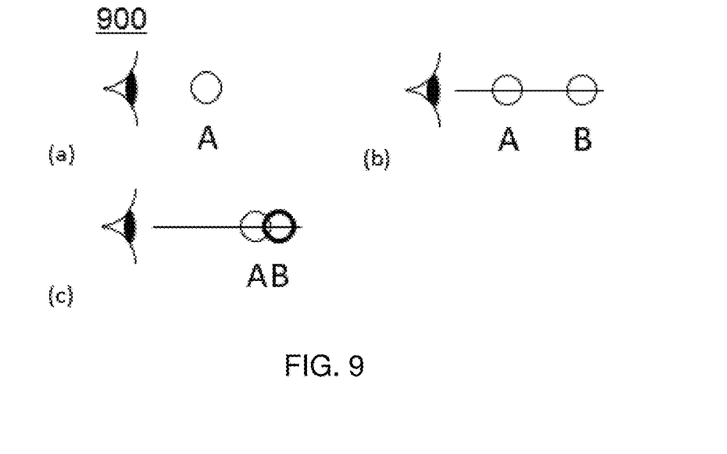
FIG. 9 depicts how a line-of-sight deletion operation works according to this disclosure.

The methodology implemented for line-of-sight deletion is shown in FIG. 9. As depicted in FIG. 9(a), assume that the camera 900 sees an object A. Later, and during scanning as depicted at FIG. 9(b), the camera sees an object B. Because object A is along the line-of-sight from the camera to B, and according to the technique herein, the algorithm considers A to be erroneous, and the weighting of A is decreased. If, however, and as depicted at FIG. 9(c), objects A and B are very close together, the geometry of the surface may be uncertain. As scanning continues (and more data is obtained), however, and as the algorithm becomes more sure about the relative positions, the weight of object B increases, and the weight of A decreases, thereby yielding a more accurate estimate of the true surface.

Immediate Deletion

In certain cases, and as also described, preferably the algorithm immediately deletes 3D samples it believes to be erroneous. The notion of "immediate" does not necessarily require a particular time requirement or limit. Samples identified for immediate deletion are simply omitted from the 3D model without the requirement of additional data collection/detection. As noted above, immediate deletion as used herein is equivalent to setting the weight of these 3D samples to zero. Preferably, immediate deletion occurs if either or both of the following situations occur. In particular, preferably existing 3D samples that intersect the body of the scanner (so-called scanner intersection) are immediately deleted. For example, this can happen if a dental user accidentally scans the patient's cheek from the lingual side of the teeth. When the dental user moves the scanner to scan the buccal side of the teeth, the cheek is displaced by the body of the scanner, and these 3D samples are deleted immediately. Another example (suitable for the immediate deletion case) is where one or more 3D samples are disconnected from the main body of 3D samples (so-called "disconnected components"). Connectivity of the 3D samples can be determined by the distance between them. A distance threshold determining connectivity may vary depending on geometry, time, or other factors. For example, a higher distance threshold may be used during scanning, and a lower distance threshold may be used during a "cleanup" operation, e.g., when active scanning stops.

Figure 10:
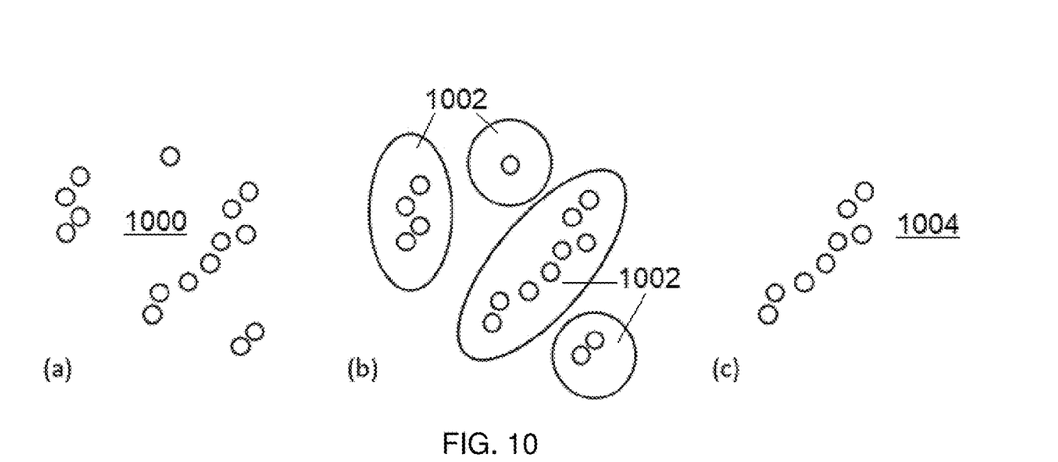
FIG. 10 depicts how one aspect of an immediate deletion operation works according to this disclosure.

The notion of determining connected components (and then deleting disconnected ones) is depicted in FIG. 10. In particular FIG. 10(a) depicts a collection of 3D samples 1000. FIG. 10(b) shows the 3D samples of FIG. 10(a) grouped into components 1002. As depicted in FIG. 10(c), all but the largest component 1004 (that is, the component with the largest number of points) have been deleted. The groupings 1002 (in FIG. 10(b)) that are not present in FIG. 10(c) represent the portions deleted by the mechanism. Preferably, the 3D samples are grouped into components by executing a sparse-connected components algorithm. The algorithm identifies the largest connected component 1004 and selectively deletes the disconnected ones.

Figure 11:
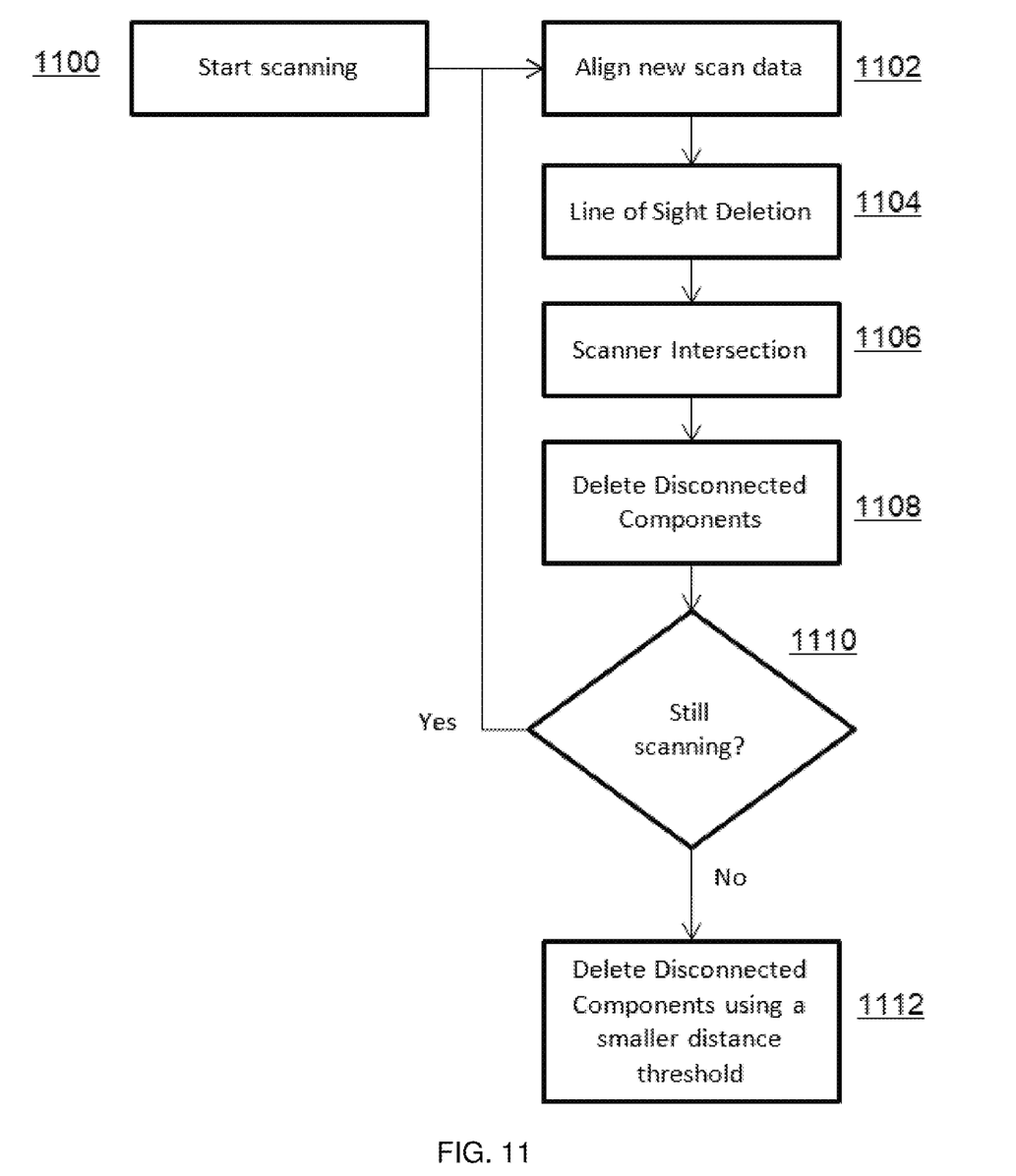
FIG. 11 depicts a representative process flow of the active delete function of this disclosure.

FIG. 11 depicts a process flow that depicts the line-of-sight (a first) deletion mechanism, and the immediate (a second) deletion mechanism. The routine begins at step 1100 when the user starts scanning, thereby collecting new 3D samples. As described, these samples must be aligned to any existing 3D samples. To that end, and at step 1102, the system aligns the new scan data. At step 1104, line-of-sight deletion is carried out. Steps 1106 and 1108 provide the immediate deletion function; in particular, at step 1106 any obvious errors (e.g., scanner intersection) are deleted, and step 1108 identifies and deletes the disconnected components. The sequence of steps 1104, 1106 and 1108 is not intended to be limiting, as these operations can occur concurrently or in some other ordering. At step 1110, a test is performed to determine if the user is still scanning. If so, control returns to step 1102. When scanning is done, further "cleanup" may be done. To that end, the routine continues at step 1112 to further delete any remaining disconnected components, preferably as measured against a more "fine-grained" distance threshold. Step 112 uses a fine-connected components algorithm. Although not shown in this process flow, the output of the active delete functionality (or individual operations thereof, such as the immediate deletion) is to used to update a rendering of the 3D model that is available to the user. Thus, the deletions themselves (if the 3D samples representing the portions identified for deletion are already on the screen) are updated in real-time on the display rendering, thereby providing a more useful and aesthetic rendering of the object or surface of interest. The manner in which the deletions are processed may vary. Further, where possible (e.g., in the case of immediate deletion) points corresponding to the 3D samples identified for deletion may simply be discarded prior to model generation.

Figure 12:
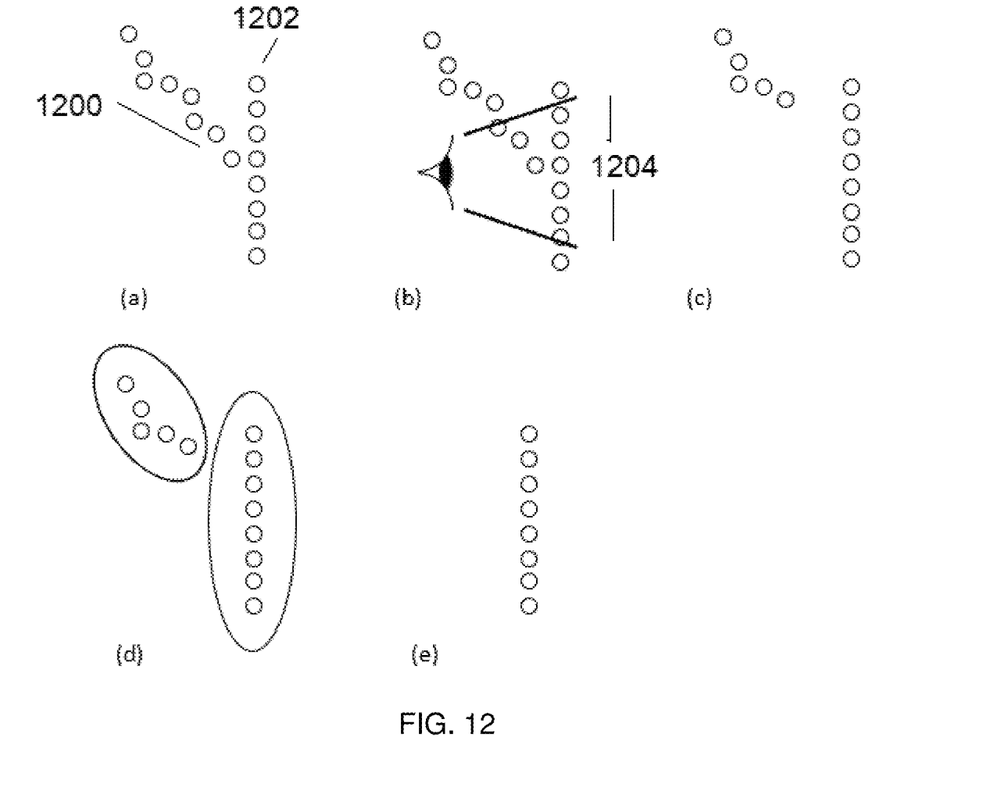
FIG. 12 depicts how the line-of-sight and immediate deletion operations work cooperatively to facilitate removal of the unwanted item.

FIG. 12 depicts an example of how the first and second delete mechanisms can be used together. In this example, and as depicted in FIG. 12(a), an item 1200 to be deleted is directly touching the "true" surface 1202; as a consequence, it is assumed that the immediate deletion mechanism (using the disconnected components algorithm) is unable to remove it. As depicted in FIG. 12(b), the size of the item to be deleted is larger than the field of view 1204 of the camera, making it also difficult or impossible for line-of-sight deletion alone to remove it. The combination of both mechanisms, however, effectively and naturally removes the item. First, and as shown in FIG. 12(c), line-of-Sight deletion removes 3D point cloud samples close to the "true" surface. This leaves the rest of the item disconnected from the true surface. As depicted in FIGS. 12(d) and (e), the remaining 3D samples of the item to be deleted are then deleted because they are determined to be a disconnected component.

The technique herein provides significant advantages. It allows removal of unwanted data scanned accidentally or otherwise present in the rendered model. The deletion (filtering) is active in the sense that it occurs in real-time, e.g., instantly/immediately with respect to items that are clear errors, such as an item that is present inside the modeled tip area, or "on-the-fly" (dynamically) as the model is being rendered and based on the algorithm's confidence (in turn based on the 3D sample weightings) that a particular item or artifact is not part of the actual object of interest.

In one embodiment, the active delete function is activated by selecting an icon on the display interface. In another embodiment, the function is activated by the user selecting and then releasing a button on the scanner itself while the scanner is in use. Once active, the user scans over the desired area and the samples identified by the line-of-sight evaluation are automatically deleted when their associated weightings fall below the thresholds. Different thresholds may be used for different 3D samples. As described, samples that are identified for immediate deletion are deleted as well, as a particular sample determined to be ready for immediate deletion has its weight adjusted to a predetermined value below the threshold (e.g., zero).

The weighting technique herein provides significant advantages. For line-of-sight deletion in particular, the weight-based approach ensures that erroneous data close to the true surface will be gradually deleted as more information is collected about the true surface geometry, thus preserving surface accuracy. In contrast, the major advantage of immediate deletion is speed: the user does not have to spend as much time scanning to delete items farther from the surface and/or items that are clearly erroneous. The line-of-sight (first) and immediate (second) mechanisms may be integrated together or separate functionality; typically, these operations are implemented as described in software, as a set of computer program instructions executing in a hardware processor.

There may been several variants to the above-described functionality in whole or in part. When running the fine-connected components algorithm, e.g., color may be masked so that the user can see that the identified points will be deleted. More generally, color may also be used to emphasize points that are more likely to be deleted. During processing, it may be desirable for the algorithm to consider a neighborhood of a voxel grid point that the algorithm is considering for deletion, and then act on data in that neighborhood; this approach will be useful for the typical case when the object identified for deletion is larger than a single grid point. In another variant, data density information may be obtained but only incorporated after scanning is complete instead of "on-the-fly," which is the preferred approach. Another variant is to increase the weighting penalty for objects that are further away from a corresponding point in the scan volume. A further possible variant is to decrease the weighting penalty for objects with normal that are orthogonal to the camera look at normal, as points with near orthogonal normal tend to have the most error. Another variant is to increase the weighting penalty for isolated points, e.g. those that do not have voxel neighbors. Still another variant is to use an active crop region, which can be defined as a minimum bounding rectangle that contains all of the points in a current scan volume; voxel points outside of this region would then be identified for deletion. In this latter approach, it may only be necessary to consider points and voxels inside the scanning frustum. Yet another variant is to delete points that have different normal than the current scan volume and that occupy a same {x, y} position in the camera plane. Another variant works as follows: for any points that the previous solutions miss, create another processing thread that continuously finds the largest connected component, and slowly weight down items that are not part of this large connected component.

Having described the invention, what we claim is as follows:

1. A method implemented in association with an intra-oral scanning device and an associated computing system executing software, the software configured to extract a three-dimensional (3D) point cloud from data captured by the intra-oral scanning device, align the 3D point cloud to previously-captured data, and render a 3D model to an associated display screen, the 3D model representing a scanned object and configured as a collection of discrete 3D samples that approximate an actual continuous surface of the scanned object, comprising:

associating a weight representing a density of data with each discrete 3D sample in at least a portion of the 3D model;
adjusting the weights of one or more of the 3D samples by:
  decreasing a weight of a 3D sample that is determined to be within a line-of-sight to a point within the 3D point cloud;
  responsive to decreasing the weight, determining whether a resulting adjusted weight of the 3D sample determined to be within the line-of-sight falls below a threshold;
  responsive to determining that the resulting adjusted weight of the 3D sample has fallen below the threshold, marking that 3D sample for deletion; and
actively deleting one or more 3D samples based at least in part on a sample's weight or adjusted weight, wherein the one or more deleted 3D samples represent an unwanted item in the rendered 3D model.

2. The method as described in claim 1 wherein the weights are adjusted during a scan.

3. The method as described in claim 1 further including updating the 3D model in real-time to render on the associated display screen without the unwanted item.

4. The method as described in claim 1 wherein adjusting the weights occurs as scanning proceeds and includes:
  identifying a particular 3D sample for immediate deletion; and
  setting the weight of the particular 3D sample to a value indicating immediate deletion.

5. A method implemented in association with an intra-oral scanning device and an associated computing system executing software, the software configured to extract a three-dimensional (3D) point cloud from data captured by the intra-oral scanning device, align the 3D point cloud to previously-captured data, and render a 3D model to an associated display screen, the 3D model representing a scanned object and configured as a collection of discrete 3D samples that approximate an actual continuous surface of the scanned object, comprising:
  associating a weight representing a density of data with each discrete 3D sample in at least a portion of the 3D model;
  adjusting the weights of one or more of the 3D samples by:
    grouping 3D samples into groupings of samples;
    identifying a largest grouping of samples, and one or more smaller groupings of samples; and
    marking for deletion the one or more smaller groupings of samples; and
  actively deleting one or more 3D samples based at least in part on a sample's weight or adjusted weight, wherein the one or more deleted 3D samples represent an unwanted item in the rendered 3D model.

6. The method as described in claim 5 wherein the adjusting occurs as a scan is proceeding.

7. The method as described in claim 6 further including, following the scan and during a cleanup operation, identifying and marking for deletion an additional grouping of samples.

8. Apparatus configured in association with an intra-oral scanning device, comprising:
a processor; and
computer memory holding computer program code executed by the processor and configured to extract a three-dimensional (3D) point cloud from data captured by the intra-oral scanning device, align the 3D point cloud to previously-captured data, and render a 3D model to an associated display screen, the 3D model representing a scanned object and configured as a collection of discrete 3D samples that approximate an actual continuous surface of the scanned object, the program code further configured to:
  associate a weight representing a density of data with each discrete 3D sample in at least a portion of the 3D model;
  adjust the weights of one or more of the 3D samples by:
    decreasing a weight of a 3D sample that is determined to be within a line-of-sight to a point within the 3D point cloud;
    responsive to decreasing the weight, determining whether a resulting adjusted weight of the 3D sample determined to be within the line-of-sight falls below a threshold;
    responsive to determining that the resulting adjusted weight of the 3D sample has fallen below the threshold, marking that 3D sample for deletion; and
  actively delete one or more 3D samples based at least in part on a sample's weight or adjusted weight, wherein the one or more deleted 3D samples represent an unwanted item in the rendered 3D model.

9. The apparatus as described in claim 8 wherein the weights are adjusted during a scan.

10. The apparatus as described in claim 8 wherein the program code is further configured to cause updating of the 3D model in real-time to render on the associated display screen without the unwanted item.

11. The apparatus as described in claim 8 wherein the program code configured to adjust the weights operates as scanning proceeds and includes program code further configured to:
  identify a particular 3D sample for immediate deletion; and
  set the weight of the particular 3D sample to a value indicating immediate deletion.

12. Apparatus configured in association with an intra-oral scanning device, comprising:
a processor; and
computer memory holding computer program code executed by the processor and configured to extract a three-dimensional (3D) point cloud from data captured by the intra-oral scanning device, align the 3D point cloud to previously-captured data, and render a 3D model to an associated display screen, the 3D model representing a scanned object and configured as a collection of discrete 3D samples that approximate an actual continuous surface of the scanned object, the program code further configured to:
  associate a weight representing a density of data with each discrete 3D sample in at least a portion of the 3D model;
  adjust the weights of one or more of the 3D samples by:
    grouping 3D samples into groupings of samples;
    identifying a largest grouping of samples, and one or more smaller groupings of samples; and
    marking for deletion the one or more smaller groupings of samples; and actively delete one or more 3D samples based at least in part on a sample's weight or adjusted weight, wherein the one or more deleted 3D samples represent an unwanted item in the rendered 3D model.

13. The apparatus as described in claim 12 wherein the adjusting occurs as a scan is proceeding.

14. The apparatus as described in claim 13 wherein the program code is further configured following completion of the scan and during a cleanup operation, to identify and mark for deletion an additional grouping of samples.

* * * * *